United States Patent [19]

Fiddian-Green

[11] Patent Number: 4,671,287
[45] Date of Patent: Jun. 9, 1987

[54] APPARATUS AND METHOD FOR SUSTAINING VITALITY OF ORGANS OF THE GASTROINTESTINAL TRACT

[76] Inventor: Richard G. Fiddian-Green, 127 Brigham Hill Rd., N. Grafton, Mass. 01536

[21] Appl. No.: 825,509

[22] Filed: Feb. 3, 1986

Related U.S. Application Data

[63] Continuation-in-part of Ser. No. 566,649, Dec. 29, 1983, Pat. No. 4,576,590.

[51] Int. Cl.[4] .................. A61M 25/00; A61B 5/00
[52] U.S. Cl. .................. 128/631; 128/1.3; 604/26; 604/54; 604/95
[58] Field of Search .................. 128/1.3–1.5, 128/632, 635; 604/24–26, 95–103, 54

[56] References Cited

U.S. PATENT DOCUMENTS

| | | | |
|---|---|---|---|
| 3,043,309 | 7/1962 | McCarthy | 604/54 |
| 3,658,053 | 4/1972 | Fergusson et al. | 128/632 |
| 3,674,014 | 7/1972 | Tillander | 128/657 |
| 3,893,448 | 7/1975 | Brantigan | 128/632 |
| 4,063,561 | 12/1977 | McKenna | 128/207.15 |
| 4,244,362 | 1/1981 | Anderson | 128/200.26 |

Primary Examiner—Dalton L. Truluck

[57] ABSTRACT

Medical treatment apparatus and method for sustaining the vitality of an organ in the gastrointestinal tract by catheterization including improvements in catheter placement, ischemia detection, and oxygenation is disclosed. In one embodiment, the catheter includes magnetically responsive material and placement of the catheter is accomplished by manipulating one or more magnetic devices.

14 Claims, 16 Drawing Figures

APPARATUS AND METHOD FOR SUSTAINING VITALITY OF ORGANS OF THE GASTROINTESTINAL TRACT

REFERENCE TO A RELATED APPLICATION

This application is a continuation-in-part of application Ser. No. 566,649, filed Dec. 29, 1983, now U.S. Pat. No. 4,576,590 issued Mar. 18, 1986.

BACKGROUND AND SUMMARY OF THE INVENTION

This invention relates generally to medical treatment apparatus and methods. More specifically, it is concerned with apparatus and methods for use in sustaining vitality of an organ in the gastrointestinal tract by catheterization. The several aspects of the invention include improvements in catheter placement, ischemia detection, and oxygenation.

The nature of human anatomy is such that each individual organ's vitality is sustained by the circulation of blood through the organ's vascular system. Each organ's vascular system is of course a part of the body's larger cardio-vascular system.

For any of various reasons the circulation, and hence oxygen delivery, to any given organ may become insufficient to sustain the full vitality of that organ. For example, partial occlusion of an artery may reduce blood flow to a point where the oxygen supply is insufficient. An occlusion, whether full or partial, may be due entirely to naturally occurring phenomenon or it may be in consequence of certain procedures. Regardless of the cause, reduced oxygen delivery can have potentially devastating effects on a patient.

As another example, surgical procedures, possibly not even directly related to a particular organ, may have an effect on the organ. For instance, in the case of certain vascular surgery procedures, it may be necessary to interrupt the blood flow to a given organ or organs during the course of procedures. External blood pumps may be used to supply the organ or organs during these procedures or else the procedures must be performed with sufficient rapidity that the temporary interruption of circulation to an organ will not produce grave consequences.

The present invention is in one respect directed to novel apparatus and methods for sustaining vitality of an internal organ in situations such as these, particularly with reference to gastrointestinal organs. With the present invention it is unnecessary to utilize external devices, such as blood pumps, in association with the vascular system. The present invention provides apparatus and methods which can be used at any desired time, for example, pre-operatively, during an operation, or post-operatively.

One important advantage over prior methods and apparatus is that the invention does not directly involve the cardiovascular system. Rather, the invention contemplates the introduction of a catheter into an organ of interest. A disclosed embodiment of catheter comprises a tube having a walled chamber structure at one end. The catheter is introduced to dispose the chamber structure against the lumen of the organ of interest. The material of the chamber is one which is freely permeable to gas but poorly permeable to liquid. The tube contains a conduit for delivering fluid to the chamber.

The catheter has a dual capability, one, to monitor incipient ischemia in the organ of interest, and two to oxygenate the organ. When the organ is being monitored for ischemia, perfusion fluid is introduced and subsequently extracted to obtain a $CO_2$ sample from the lumen of the organ. The $pCO_2$ measurement is utilized to calculate the organ's pH. The calculated pH can be used as an indicator of incipient ischemia.

When the catheter is being used for organ oxygenation, oxygen is perfused through the chamber via the tube from an external source. The external source may comprise any suitable means to create an oxygen partial pressure gradient between the interior of the chamber and the lumen of the organ whereby oxygen can diffuse through the wall of the chamber and into the organ. Carbon dioxide gas generated by the organ can also diffuse through the wall of the chamber to be conveyed back through the tube for removal.

In the disclosed embodiment, the chamber and tube are so constructed and arranged as to create an axial flow along the interior of the wall of the chamber along substantially the full length of the chamber. This promotes the maximum area availability for delivering oxygen to an organ, particularly in the case where the organ is in the gastrointestinal tract. The diameter of the chamber is less than that of the organ so that the catheter does not block passage through the organ. The invention also contemplates the use of agents such as the use of vasodialator to enhance oxygenation locally and the use of blood and/or blood substitutes for oxygen-bearing purposes.

The invention also provides for improved catheter placement through the use of an auxiliary placement device in association with the catheter. An endoscope may be used as the auxiliary placement device. A disclosed embodiment of catheter has magnetically responsive structure at its tip, and the auxiliary device has an electromagnet which is cooperatively associated with the magnetic tip. The auxiliary device is operated to maintain electro-magnetic attraction of the magnetic tip structure during an initial phase of the placement process. The auxiliary device is relatively stiffer than the catheter and is used to force the catheter tip past the pylorus when the catheter is introduced into the intestines from the stomach. Thereafter a separate external magnet is used to attract the catheter tip, the electromagnet is de-energized, and the auxiliary device withdrawn. Final placement of the catheter is attained through manipulation of the external magnet.

The foregoing features, advantages and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

DESCRIPTION OF THE PREFERRED EMBODIMENT

Figure 1:
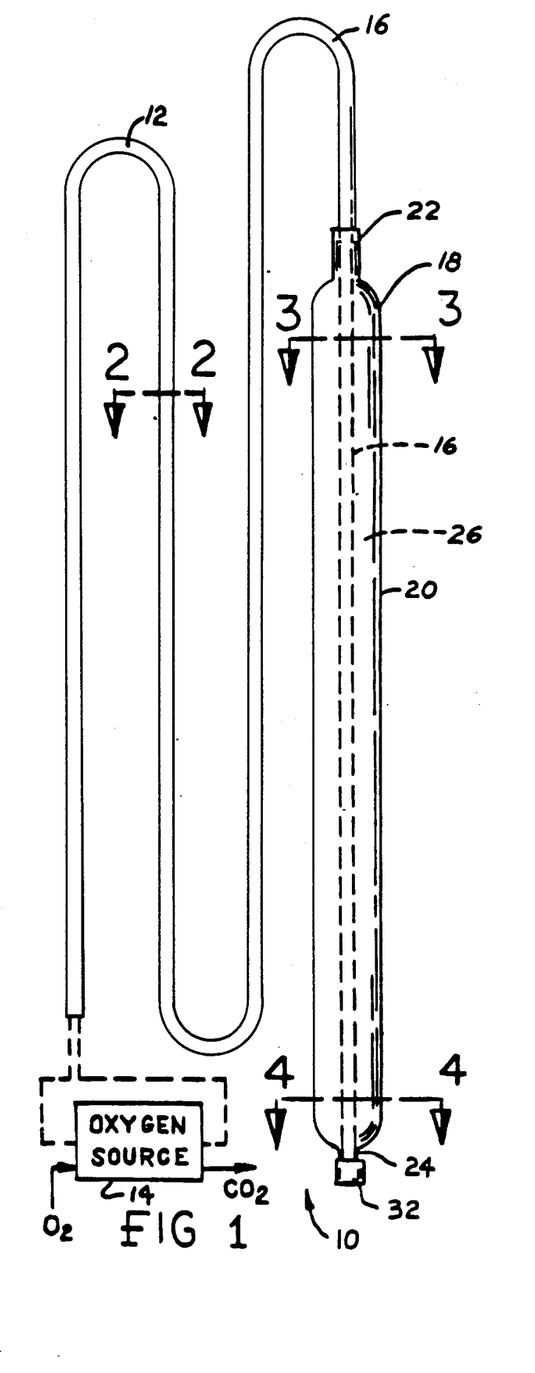
FIG. 1 is a view, partly schematic, illustrating apparatus for practice of the present invention.
Figure 2:
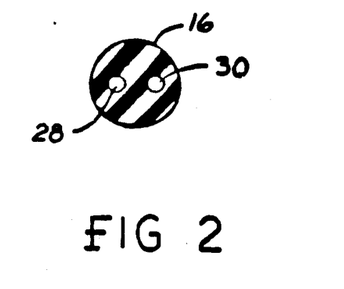
FIGS. 2, 3, and 4 are enlarged transverse cross sectional views taken in the direction of arrows 2—2, 3—3, and 4—4 respectively in FIG. 1.

FIG. 1 illustrates an exemplary embodiment of apparatus 10 for practice of the invention for organ oxygenation. Apparatus 10 comprises a catheter designated by the general reference numeral 12. Associated with catheter 12 is any suitable oxygen source designated by the general reference numeral 14.

Catheter 12 comprises a tube 16 on the distal end of which is disposed a walled chamber 18. The opposite proximal end of tube 12 is adapted for connection with apparatus 14.

Chamber 18 is provided by a tubular element having a nominal diameter greater than that of tube 16. FIG. 1 illustrates a representative shape but the invention is not limited to the particular shape or proportions illustrated. The tubular element 20 constitutes a membrane which forms chamber 18 and is fitted over the distal end of tube 16. The opposite axial ends of element 20 are closed onto the outside of tube 16 as at 22 and 24. In this way the chamber 18 defines an annular space 26 around the outside of tube 16.

Tube 16 is a soft pliable material, silicone for example, which has a circular cross sectional shape. Tube 16 is provided with a pair of axially extending conduits, or passages, 28 and 30 respectively, these extend the full length of the tube and the catheter includes any suitable closure means, for example an end closure element 32 to close off the distal end of the tube for the purpose of closing conduits 28 and 30 at that end.

Figure 3:
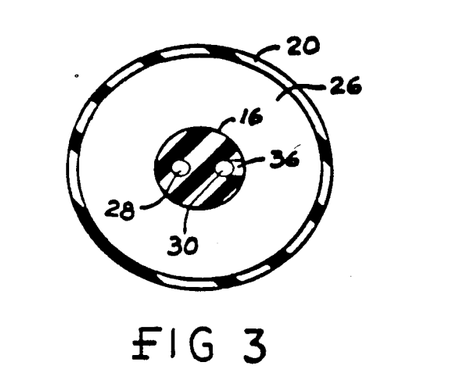
Figure 4:
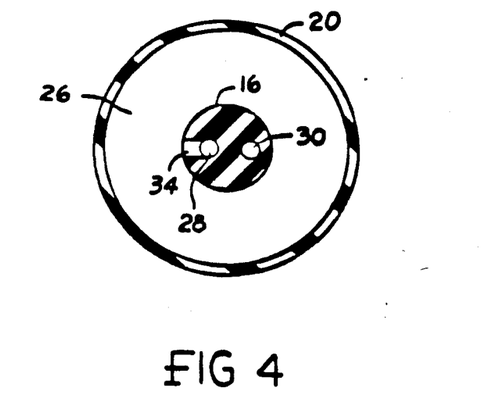

Conduits 28 and 30 are communicated with the interior chamber space 26 by means of respective apertures 34 and 36 as shown in FIGS. 4 and 3 respectively. Each aperture is provided as a transversely extending hole from the exterior of the wall of tube 16 to intercept the corresponding conduit as shown in the drawing figures.

In use oxygen is introduced into one of the two conduits and conveyed through tube 16 to exit the tube at the corresponding aperture into chamber space 26. The interior of the chamber space is thereby perfused with oxygen. The opposite aperture provides for return conveyance of gases via the other conduit through tube 16.

Hence, if oxygen is introduced into conduit 28, it will flow through that conduit, exit via aperture 34 and pass into the far distal end of chamber space 26. The flow will continue axially through the annular chamber space 26 toward the proximal end of the chamber to enter aperture 36 and subsequently pass via conduit 30 back through tube 16.

If the direction of flow were to be reversed, flow through chamber space 26 would be distally, exiting tube 16 at aperture 36, passing axially through the chamber space to re-enter tube 16 at aperture 34 for return via tube 16.

In accordance with principles of the invention, the material of tube 20 is one which is freely permeable to gas but poorly permeable to liquid, so that tube 20 is a membrane. A suitable material is polydimethylsiloxane which is freely permeable to oxygen and carbon dioxide gases. The oxygen in the catheter chamber has a partial pressure so that oxygen can diffuse through the wall of the chamber 18.

In use, catheter 12 is introduced into a patient such that chamber 18 is placed against the lumen of the hollow internal organ of interest. The elongate shape illustrated in FIG. 1 is intended for placement in the gastrointestinal tract, particularly the intestines. The placement may be made preoperatively or intraoperatively, and the catheter may remain in place even into a postoperative period.

Apparatus 14 is of any suitable configuration which is capable of perfusing oxygen through tube 16 and chamber 18 at a suitable partial pressure. For example, the apparatus may comprise a standard hospital oxygen supply giving a pressure of 760 mm.Hg. It could also alternately comprise a pump which delivers oxygen-enriched fluid. For example, the fluid may be a saline solution which is pumped by the pump through the catheter with provisions being made for oxygenating the saline solution prior to introduction into the catheter so that the fluid bears a dissolved oxygen gas at suitable partial pressure.

With the wall of chamber 18 being placed against the lumen of an internal organ, the flow of oxygen axially along the interior of the wall of tube 20 creates a condition whereby oxygen can diffuse through the wall of tube 20 and into the lumen of the organ. The diameter of chamber 26 is less than that of the organ so that the catheter does not block flow through the tract. In this way, oxygen may continue to be supplied to the organ so as to sustain its vitality under conditions which otherwise might render the organ moribund. Because the organ will also generate carbon dioxide gas as a waste product, that waste gas can diffuse from the lumen through the wall of tube 20 and into the fluid which is being conveyed through chamber space 26.

The carbon dioxide gas is conveyed from chamber space 26 with the exiting fluid flow which passes proximally through tube 16 to the proximal end. In this way not only is oxygen made available to the organ but a waste product from the organ is also removed.

Depending upon the degree of sophistication of apparatus 14 the carbon dioxide may be removed from the fluid and the fluid recirculated so as to form a closed system or otherwise the apparatus may be an open system in which the fluid which returns from tube 16 is discarded.

In order to sustain vitality of the intestine, the $PO_2$ of the oxygen introduced into chamber 26 must be high enough to create a certain gradient across the wall of the chamber and the lumen of the organ. In the lumen of a healthy intestine the $PO_2$ is about 100 mm.Hg. If the organ becomes ischemic, this figure drops to about 60 mm.Hg. Therefore, the $PO_2$ of the fluid delivered to the catheter should certainly exceed 100 mm.Hg. At the present time the use of 760 mm.Hg. oxygen gas as the sole fluid introduced into the catheter appears to be very effective. The return flow is merely exhausted.

The invention is also preferably practiced such that the material of tube 20 is not significantly stretched, or expanded, when in use, so that blockage of the passage through the tract may be avoided.

The material of tube 20 will be permeable to molecules having molecular weights of less than about 3000. Therefore, it is also possible to use the catheter to introduce drugs, nutrients, and/or other agents having molecular weights of less than about 3000.

Certain agents enhance the effectiveness of the procedure. For example it is possible to introduce a vasodialator via the catheter to enhance the local oxygenation. It is also contemplated that blood or blood substitutes could be used in an oxygen-bearing fluid to enhance the oxygen carrying capacity.

A significant advantage of the invention is that it is unnecessary to directly involve the circulatory system for practice of the invention. Thus, the invention is different in principle from prior vascular oxygenation procedures which merely oxygenate the blood. With the invention, oxygen is made available directly to the lumen of the organ. The oxygen so delivered may be assistive of the current vascular flow, or it may be the sole source of oxygen.

The present disclosure illustrates one preferred embodiment of the invention in a form which is especially useful for the intestine. Other embodiments and forms are contemplated within the scope of the invention. For example, the catheter could be constructed with a full nasoanal extent through the tract with oxygen being introduced at one end and the flow being discharged at the opposite end.

The invention has been shown to provide for perfusion of oxygen through a hollow internal organ of the gastrointestinal tract independently of the vascular system. The oxygen so delivered may be assistive of current blood flow to the organ or it may be the sole source. While the invention may be practiced alone, it may also be practiced in conjunction with other procedures. The perfusion is accomplished with direct oxygen delivery to the lumen of the organ in a controlled manner without blockage of the tract.

A further aspect of the invention comprises the capability of selectively operating the catheter to monitor for incipient ischemia of the organ of interest and to oxygenate the organ. Briefly, when an organ is being monitored for incipient ischemia, aspirating fluid is introduced, equilibrated, and subsequently extracted to obtain a $pCO_2$ sample from the lumen of the organ. The $pCO_2$ measurement is utilized in calculating the organ's pH. Calculation of pH is performed using conventional procedures relating the $pCO_2$ measurement to the bicarbonate concentration in arterial blood. The pH measurement is used as an indicator of incipient ischemia.

Figure 5:
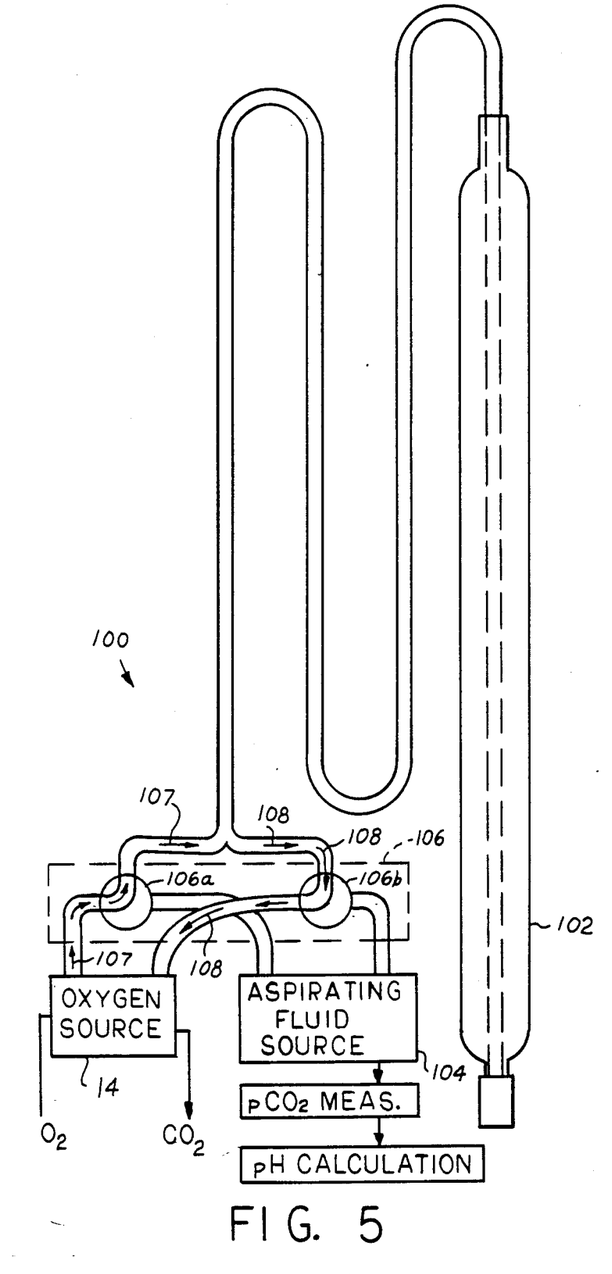
FIG. 5 is a view, partly schematic, illustrating another form of apparatus for practice of the present invention.

FIG. 5 illustrates an exemplary apparatus 100 for practicing this further aspect of the invention. The apparatus 100 includes a catheter 102 which is essentially like catheter 12 of FIGS. 1–4. A detailed description of catheter 102 will therefore not be given.

A principal difference in the apparatus 100 versus apparatus 10 described in FIGS. 1–4 involves equipment external of the catheter. This equipment in apparatus 100 provides for the dual capability of monitoring-/oxygenating.

Apparatus 100 comprises in addition to the oxygen source 14, an aspirating fluid source 104. The two sources 14 and 104 are operatively coupled with catheter 102 by a valve mechanism, generally 106. Valve mechanism 106 comprises two separate valve devices 106a, 106b and each valve device has three ports and is selectively operable to at least two different positions. Preferably the two valve devices are connected to a common operator for ganged operation in unison.

In the position shown in FIG. 5 the valve devices 106a, 106b serve to connect oxygen source 14 to the catheter tube so that the same type of circuit exists as in FIG. 1. In this position oxygen perfusion fluid can pass through valve device 106a, and into the catheter. The return flow is via valve device 106b. This flow is depicted by the small arrows 107 for the entrance flow into the catheter and the arrows 108 for the exit flow from the catheter. At this time there are no flow paths from the aspirating fluid source 104 to the catheter, and accordingly oxygen perfuses the organ of interest to assist in sustaining its vitality.

When the two valve devices are operated to a second position, the aspirating fluid source 104 is connected to the catheter while the oxygen source 14 is disconnected. This is done for example by rotating the valving portions of the two valve devices 90° in the clockwise direction as viewed in FIG. 5. In this second position, flow from aspirating fluid source 104 passes through valve device 106a and into the catheter. The return flow from the catheter is through valve device 106b back to aspirating fluid source 104.

The purpose of introducing aspirating fluid into the catheter is to obtain a sample of $CO_2$ gas generated by the organ of interest for the purpose of securing a $pCO_2$ measurement. There are various techniques for obtaining the $pCO_2$ measurement and one way is to introduce a certain amount of aspirating fluid into the walled catheter chamber and leaving it there for a sufficient amount of time to allow $CO_2$ gas to diffuse from the organ's lumen, through the permeable wall of the catheter chamber, and into the aspirating fluid and equilibrate. For example, ½ hour may be suitable in certain applications. The aspirating fluid is then withdrawn from the catheter and is subjected to analysis such as for example, by a conventional gas analyzer to measure the $pCO_2$.

A measurement of the bicarbonate concentration in arterial blood of the patient is also obtained, and these two measurements are then used to calculate the pH of the organ of interest. Such measurements may be taken at periodic intervals and in this way a record of pH values can be established.

A certain change in pH is indicative of incipient ischemia, and therefore when such a potentially devastating condition is detected, the apparatus may then be operated to oxygenate the organ in an effort to counter the ischemic tendency. In this way apparatus 100 may be selectively used for its dual capability of monitoring-/oxygenating.

Figure 6:
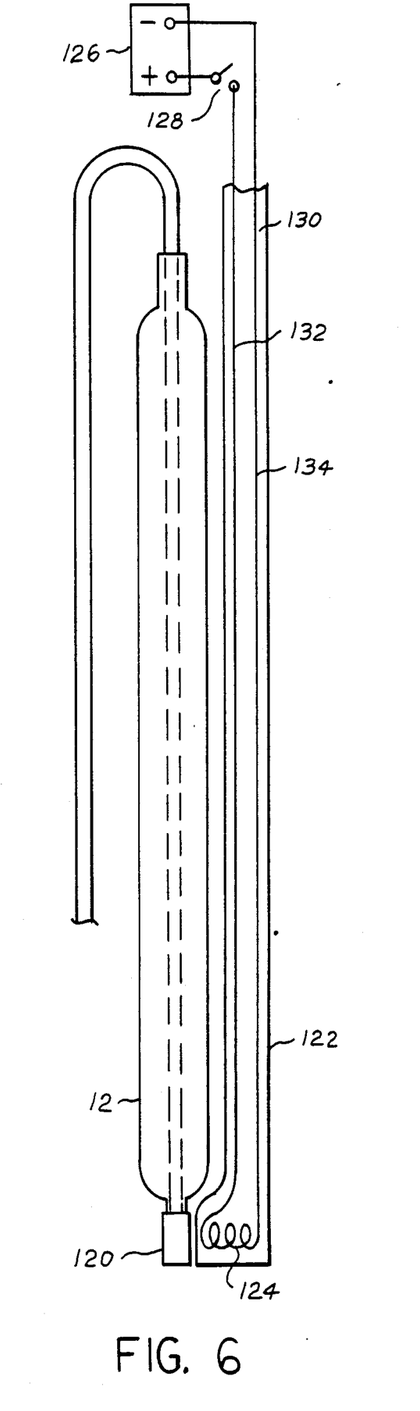
FIG. 6 is a view similar to FIG. 5 showing a further modification.

FIG. 6 illustrates a still further aspect of the invention which facilitates catheter placement. It is useful with both catheters 12, 102 and other forms of catheters as well. One of the major difficulties in successfully employing a gastrointestinal catheter is that of placement into the tract. In order for such a catheter to conform to the tract while creating as little discomfort as possible it is desirable that the catheter be a soft, pliable bio-compatible material, such as that described earlier. Unfortunately a soft, pliable elongate member is inherently difficult to place into the tract. Making the catheter stiffer for placement purposes is counterproductive to the need for having a soft, pliable construction. Therefore, the aspect of the invention which will be described with reference to the remaining drawing FIGS. 6–10 relates to a solution to this problem.

The catheter is provided with a magnetic medium, for example on the tip end, as shown at 120 in FIG. 6 for catheter 12. A separate, elongate, auxiliary placement device 122 is utilized in association with the catheter and comprises an electro-magnet 124 at the distal end which is adapted to be selectively energized from an external source at the proximal end. The external source is shown to comprise a battery 126 connected through a series on-off switch 128 to electro-magnet 124. When switch 128 is closed, the electro-magnet is energized, and when the switch is open, the electro-magnet is de-energized.

The elongate device 122 comprises an elongate body 130 of relatively greater rigidity than the catheter itself. Preferably the conductive wires 132, 134 leading to the electro-magnet are embedded within this body, as is the electro-magnet. The external surface of the body is preferably smooth and bio-compatible.

Placement is accomplished by placing the electro-magnet adjacent the tipped end of the catheter, and energizing the electro-magnet to unite the catheter and the placement device at their distal ends. They are then introduced into a patient, for example via nasal introduction.

Figure 7:
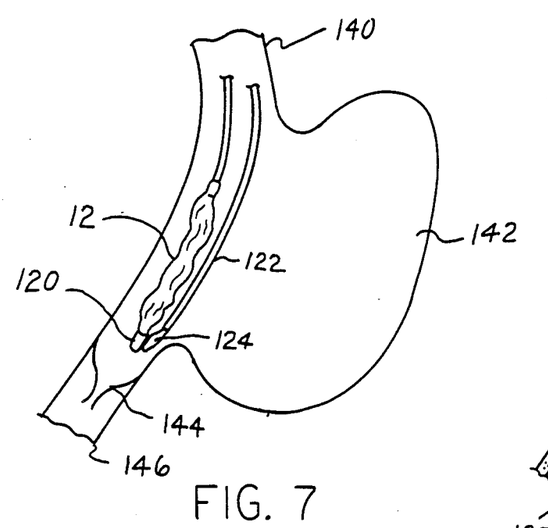
FIGS. 7, 8, 9, and 10 are respective views illustrating representative method steps for practicing one embodiment of the invention.

FIG. 7 shows the catheter and placement device having been passed through the esophagus 140 and into the stomach 142. The placement device has sufficient rigidity so that it can be forced into the tract, and by virtue of magnetic coupling with the catheter, pull the catheter along with it.

Figure 8:
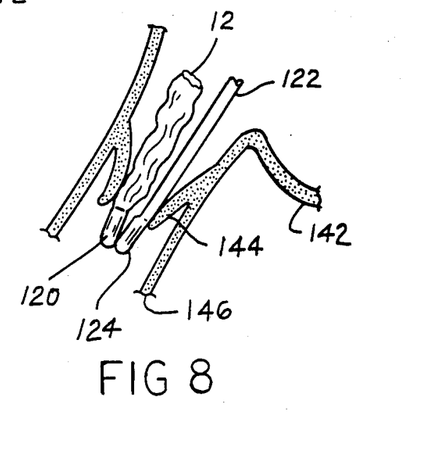
Figure 9:
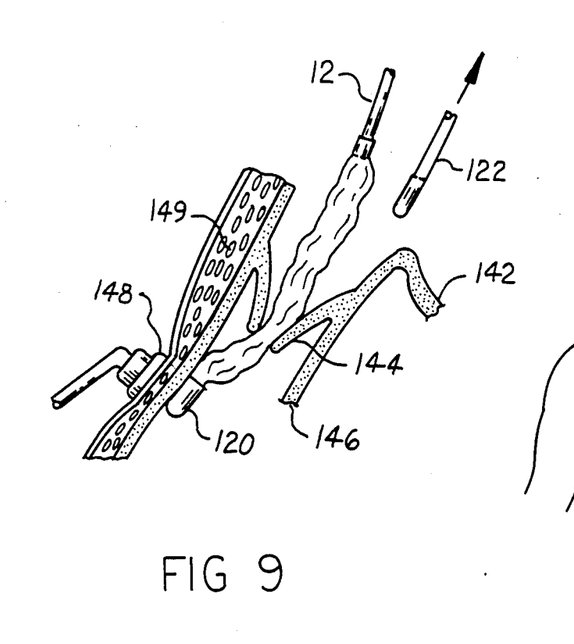

A particular difficulty in catheter placement is typically encountered at the pylorus 144. The auxiliary placement device can be used to force the pylorus open so that both it and the catheter pass through the pylorus and into the small intestine 146, This is shown in FIG. 8. Once the pylorus has been passed, the next problem encountered is to successfully withdraw only the electro-magnet, and this is where a further aspect of the invention becomes particularly significant. Since the pylorus keeps tending to reject the intruding apparatus, a counter-force is inherently being applied to the apparatus. This further aspect of the invention is shown in FIG. 9 and involves placing a strong magnet 148 externally of the intestine at the vicinity of the catheter's tip end. FIG. 9 shows magnet 148 extra-operatively acting through the patient's abdomen 149. This external magnet has sufficient strength to hold the tip of the catheter in place while the electro-magnet 124 is de-energized and the auxiliary device 122 is then withdrawn. Because of its nature electro-magnet 124 will not be significantly attracted to the external magnet when de-energized. Yet, the strength of the external magnet will hold the tip end of the catheter in place so that upon withdrawal of the auxiliary device, only the soft pliable catheter is left in place.

Figure 10:
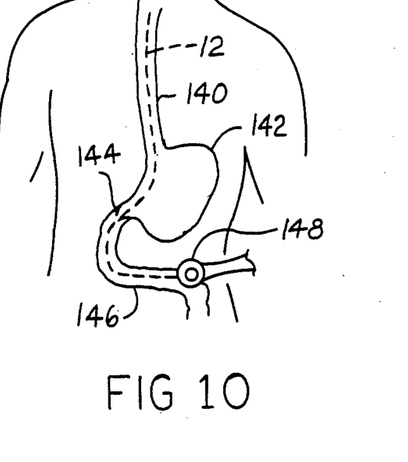

If the catheter is in a suitable position by virtue of its placement by device 122, then no further manipulation of the external magnet 148 need be done. It is contemplated however that further catheter placement may be required, and this can be done by a suitable manipulation of magnet 148 to move the catheter to the desired placement site. This further manipulation is shown by FIG. 10.

It can therefore be appreciated that significant facility is given to the attending physician in placement of a catheter. Once the catheter has been placed, procedures such as those described above with reference to FIGS. 1-4 and FIG. 5 may be conducted when catheters of those types are employed. The placement procedure is however applicable to other types of catheters, and other devices, duodenal feeding tubes for example. Advantageously, the auxiliary placement device 122 could be a fibro-optic endoscope designed to contain the electro-magnet and wires.

Figure 11:
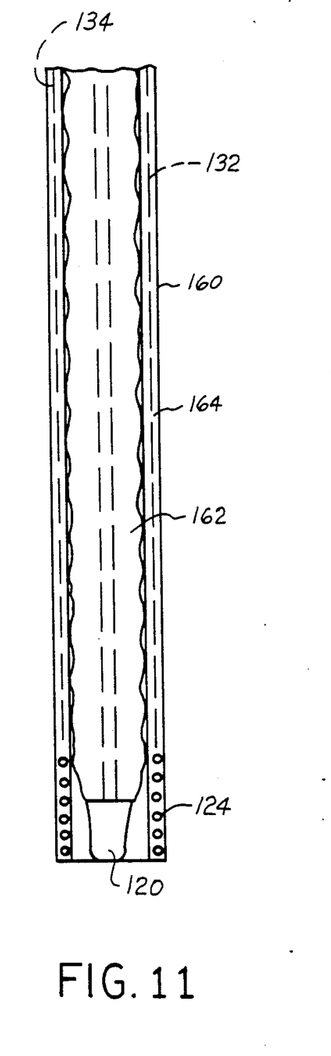
FIG. 11 shows another form of catheter.

FIG. 11 portrays another form of apparatus 160 which is similar to the apparatus of FIG. 6. Apparatus 160 comprises a catheter 162 which corresponds to catheter 12 but is disposed within a hollow tubular placement device 164 corresponding to placement device 122. FIG. 11 is of a somewhat schematic nature for purposes of illustrating this alternate configuration. The electro-magnet 124 is a coil which is disposed at the distal end of the tubular placement device 164. The lead wires from the electro-magnet extend through the placement device. The catheter 162 contains a magnetic tip end 120. The same steps described earlier are used to effect placement of catheter 162 by placement device 164.

Figure 12:
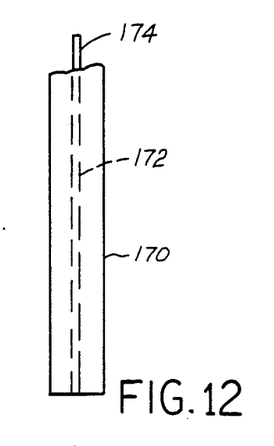
FIG. 12-16 illustrate another sequence of method steps using a further form of catheter.
Figure 13:
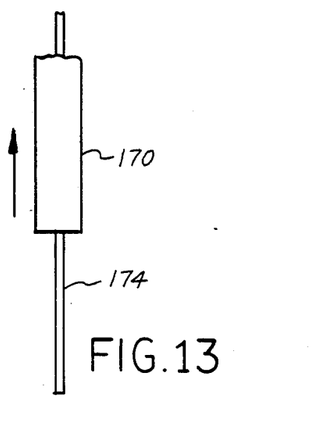

FIGS. 12-16 show schematically a sequence of steps for catheter placement but using a modified form of apparatus. In FIG. 12 an endoscope 170 has a longitudinal passage 172 containing a guidewire 174. The combination of 170 and 174 is introduced into the patient, as in the same manner described above.

Upon having achieved a desired amount of introduction (the distal end having passed the pylorus for example), the endoscope 170 is withdrawn while the guidewire 174 remains in place. (See FIG. 13.) It is contemplated that endoscope withdrawal can be accomplished by an external manipulation so that the guidewire need not necessarily be made magnetically responsive; however, as an aid to assuring that the guidewire remains in place, or at least a portion of it, such as the distal end, can be magnetically responsive so that the procedures described earlier can be used to hold the guidewire in place while endoscope 170 is withdrawn.

Figure 14:
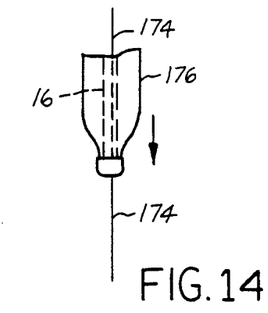
Figure 15:
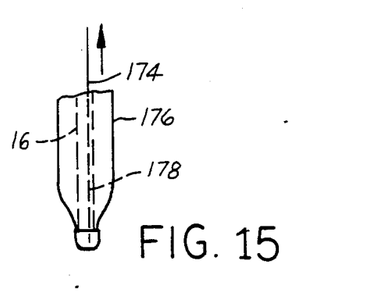

After the endoscope has been withdrawn, a catheter 176 essentially like catheter 12 is introduced (see FIG. 14). Catheter 176 may be like catheter 12, but includes a passage 178 which allows it to be guided along the in-place guidewire 174. The illustrated embodiment shows the passage 178 as being formed as its own lumen in the wall of the tube 16 so that there is no interference with the cooperative relationship of the other parts of the catheter.

Figure 16:
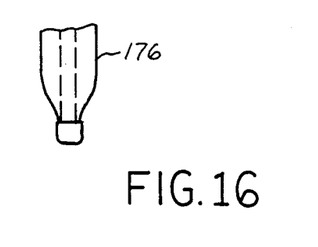

When the desired catheter placement has been obtained (see FIG. 15), guidewire 174 may be withdrawn leaving the catheter alone in place (FIG. 16). The catheter tip is magnetically responsive so that it can either be held in place as the guidewire is withdrawn and/or used for further catheter placement by manipulation of magnet 148. By suitable design, the external magnet 148 may result in a larger holding force being applied to the magnetically responsive catheter tip than to the guidewire, assuming the latter is magnetically responsive, whereby the catheter will remain in situs as the guidewire is withdrawn despite some magnetic force acting on the guidewire.

FIGS. 11-16 have described different apparatus and procedures for placement. However both catheters 162, 176 embody the same principles as catheter 12 whereby after placement the oxygenation and/or monitoring procedures described in connection with catheter 12 can be performed.

The foregoing description has disclosed principles of the invention, in its several aspects, with reference to certain embodiments and steps. Principles may be practiced in embodiments and steps other than the apparatus and steps specifically shown and described. The catheters may be introduced either through the anus into the colon or nasally in the manner described and illustrated in FIGS. 7-10. Certain steps may be performed extra-operatively or intra-operatively, and one example of an intra-operative step would be the use of an external magnet against the outer aspect of the intestines to facilitate catheter placement during a surgical procedure. FIGS. 9 and 10 portray extra-operative placement. The external magnet 148 can be a permanent magnetized piece of magnetic material, or it can be an electro-magnet which is selectively energizable. The illustrated configuration of the magnetic material on the catheter tip and the use of a single electro-magnet on the auxiliary placement device are also considered to be representative. It is possible to have multiple magnetic media on the catheter, for example at different locations, and to endow the auxiliary placement apparatus with more than one electro-magnet. While the distal end of the catheter is deemed to be the most appropriate location for the magnetic material, it will be appreciated that other placement locations may be used. Also the magnetically responsive medium on the catheter could be a magnet or an electro-magnet instead of merely a magnetically responsive piece of material.

What is claimed is:

1. A method for placement of a soft pliable catheter within an organ of the gastrointestinal tract comprising providing magnetically responsive means on the catheter, providing a placement device which is relatively more rigid than the catheter and includes a selectively energizable electro-magnet, energizing the electro-magnet and placing it to attract the magnetically responsive means of the catheter, introducing the catheter and the placement device into a patient, while the catheter remains attracted magnetically to the placement device, by forcing the placement device into the tract so that the placement device draws the catheter along with it, moving the placement device to place the catheter at a particular location in the tract, placing an external magnet at the vicinity of the magnetically responsive means of the catheter so that the magnetically responsive means is attracted to the external magnet, de-energizing the electro-magnet of the placement device, and then while the external magnet maintains an attractive force on the magnetically responsive means of the catheter, withdrawing the placement device while the catheter remains at the particular location.

2. The method set forth in claim 1 including the further step of further manipulating the external magnet after the placement device has been withdrawn so as to move the catheter to a location different from said particular location.

3. A method for selective monitoring/oxygenating of a tubular internal organ of the gastrointestinal tract which comprises introducing a catheter having a closed cylindrical walled chamber on a tube into the organ so as to dispose the wall of the chamber in contact with and against the lumen of the organ, said tube having an entrance to and an exit from said chamber, the wall of said chamber comprising a material which is freely permeable to gas but poorly permeable to liquid, then selectively obtaining via the exit from said chamber and through the tube a sample representative of a given blood gas passing from the lumen of the organ through the wall of said chamber, for analysis to monitor for incipient ischemia, and perfusing the interior of the chamber via said tube and said entrance to the chamber with oxygen to create a pressure gradient between the chamber and the lumen of the organ so as to cause oxygen to diffuse through the wall of the chamber to the lumen of the organ.

4. Apparatus for placement of, and in combination with, a soft pliable catheter within an organ of the gastrointestinal tract comprising a magnetically responsive means on the catheter and a placement device which is relatively more rigid than the catheter and includes a selectively energizable electro-magnet in cooperative association with the magnetically responsive means on the catheter so that when the electro-magnet is energized the catheter is attracted to it and when the electro-magnet is de-energized the catheter can be separated from it, said location of magnetic attraction of the placement device to the catheter being such that the placement device is effective upon introduction into the tract to draw the catheter into the organ.

5. Apparatus for selective monitoring/oxygenation of a tubular internal organ of the gastrointestinal tract comprising a catheter having a closed cylindrical walled chamber on a tube for disposition against the lumen of the organ, said tube having an entrance to and an exit from said chamber, the wall of said chamber comprising a material which is freely permeable to gas but poorly permeable to liquid, an oxygen perfusion source, an aspirating fluid source, and means for selectively connecting said oxygen perfusion source and said aspirating fluid source to said catheter so that when the oxygen perfusion source is connected to the catheter, oxygenation of the organ can be performed via said entrance to the chamber, and when the aspirating fluid source is connected to the catheter aspirating fluid can be introduced to obtain a sample of a blood gas from the lumen of the organ via the exit from the chamber.

6. The apparatus of claim 5 wherein the tube has a pair of conduits therein, with said entrance to the chamber being provided by an aperture in one conduit and wherein said exit from the chamber is provided by an aperture in another conduit.

7. The apparatus of claim 6 wherein said exit and entrance are spaced from each other axially along the length of the tube.

8. A method for placement of a soft pliable catheter with an organ of the gastrointestinal tract comprising introducing the catheter into the tract with the aid of a placement device which is separable from the catheter, providing a magnetically responsive means on the catheter, placing an external magnet at the vicinity of the magnetically responsive means of the catheter when the catheter has been introduced to a desired situs, then, while the external magnet maintains an attractive force on the magnetically responsive means of the catheter, withdrawing the placement device while the catheter remains at the desired situs; and using the same catheter to selectively oxygenate the organ or obtain a sample of a gas from the organ without withdrawing the catheter.

9. A method as set forth in claim 8 in which said placement device comprises a selectively energizable electro-magnet and said electro-magnet is energized to magnetically attract the magnetically responsive means of the catheter as the catheter and the placement device are simultaneously introduced.

10. A method as set forth in claim 9 including the further step of de-energizing the electro-magnet of the placement device when the catheter has been placed at the desired situs by the placement device.

11. A method as set forth in claim 8 in which said placement device comprises a guidewire and said catheter includes a passage via which the catheter is guided along the guidewire.

12. A method as set forth in claim 11 in which the guidewire is placed into the patient previous to the insertion of the catheter on the guidewire.

13. A method set forth in claim 12 in which the guidewire is placed into the patient by another placement device which is withdrawn from the patient after the guidewire has been placed.

14. A catheter comprising a soft pliable tube for introduction into the gastrointestinal tract, a walled sampling chamber on the tube comprising a wall of material which is freely permeable to gas but poorly permeable to liquids, said sampling chamber being in communication with said tube so that fluid can be introduced into said chamber via said tube, a magnetically responsive means on said catheter providing for electro-magnetic attraction with an electro-magnetic influence which is external to the catheter, and means extending lengthwise through the tube and being surrounded by said wall for receiving a guidewire for guiding the catheter into a desired location in the tract.

* * * * *